(12) United States Patent
Teslenko et al.

(10) Patent No.: US 9,943,671 B2
(45) Date of Patent: Apr. 17, 2018

(54) PERCUTANEOUS APPLICATION SYSTEM

(75) Inventors: Alexander Teslenko, Hagen (DE);
Dieter Gulik, Hamburg (DE);
Friedrich Von Hahn, Hamburg (DE)

(73) Assignee: MedDrop Technology AG, Thundorf (CH)

( * ) Notice: Subject to any disclaimer, the term of this patent is extended or adjusted under 35 U.S.C. 154(b) by 414 days.

(21) Appl. No.: 13/821,428

(22) PCT Filed: Sep. 7, 2011

(86) PCT No.: PCT/EP2011/004497
§ 371 (c)(1),
(2), (4) Date: Aug. 29, 2013

(87) PCT Pub. No.: WO2012/031747
PCT Pub. Date: Mar. 15, 2012

(65) Prior Publication Data
US 2013/0338610 A1 Dec. 19, 2013

(30) Foreign Application Priority Data

Sep. 8, 2010 (DE) .................. 10 2010 044 674

(51) Int. Cl.
| | |
|---|---|
| *A61K 9/08* | (2006.01) |
| *A61K 31/00* | (2006.01) |
| *A61K 9/19* | (2006.01) |
| *A61K 31/337* | (2006.01) |
| *A61M 35/00* | (2006.01) |
| *A61K 9/00* | (2006.01) |

(52) U.S. Cl.
CPC ......... *A61M 35/003* (2013.01); *A61K 9/0021* (2013.01)

(58) Field of Classification Search
CPC ................................. A61M 35/003
See application file for complete search history.

(56) References Cited

U.S. PATENT DOCUMENTS

| | | | |
|---|---|---|---|
| 5,833,891 A * | 11/1998 | Subramaniam | A61K 9/1676 264/12 |
| 2008/0038298 A1* | 2/2008 | Barnikol-Keuten | A61M 35/003 424/400 |

(Continued)

*Primary Examiner* — Todd J Scherbel
*Assistant Examiner* — Sara Sass
(74) *Attorney, Agent, or Firm* — Berliner & Associates (57) ABSTRACT

The invention relates to an application system for the transepidermal surface administration of medications, said system comprising a container (1) accommodating a sprayable, active agent-containing composition, a propellant gas source (3) for pressurized gas consisting of at least 25% v/v of oxygen, and a spraying device (2), wherein container (1), propellant gas source (3), and spraying device (2) are flow-connected with each other in such a manner that the propellant gas atomizes the sprayable composition and, when the spraying device (2) is actuated, forces it out of the spraying device (2), with the composition being forced out of the spraying device (2) in the form of a conical spray jet at an exit velocity of ≥100 m/s. With the help of the inventive application system active agents can be effectively administered via the skin without causing injury to the skin. As a result of the high exit velocity the penetration rate is especially favorable even when larger molecules are introduced.

20 Claims, 2 Drawing Sheets

(56) References Cited

U.S. PATENT DOCUMENTS

| | | | |
|---|---|---|---|
| 2008/0075649 A1* | 3/2008 | Hung | B01J 19/088 423/335 |
| 2010/0111846 A1* | 5/2010 | Boyden | A61K 9/0019 424/1.29 |
| 2010/0298760 A1* | 11/2010 | Olle | A61M 37/0015 604/20 |
| 2012/0143152 A1* | 6/2012 | Hunter | A61B 5/0059 604/298 |

* cited by examiner

Fig. 1

Fig. 2

PERCUTANEOUS APPLICATION SYSTEM

The invention relates to an application system for the transepidermal surface administration of pharmaceutical or cosmetic active agents, said system comprising a container accommodating a sprayable, active agent-containing composition, a propellant gas source for pressurized gas consisting of at least 25% v/v of oxygen, and a spraying device, wherein container, propellant gas source, and spraying device are flow-connected with each other in such a manner that the propellant gas atomizes the sprayable composition and forces it out of the spraying device when the spraying device is actuated.

The skin is the largest organ of a human being and inter alia serves as barrier preventing the ingress of noxious substances and pollutants, in particular disease-causing agents from the environment. From an anatomical viewpoint the skin is a multi-layer organ. To the outside, the skin ends in the epidermis (upper skin), a keratinizing multilayered squamous epithelium free of blood vessels which has an outer corneal layer (stratum corneum). The dermis (true skin) is the layer beneath the epidermis. Located beneath the dermis is the subcutis (subcutaneous fatty tissue). Embedded in the skin are perspiratory glands, sebaceous glands, and hair. It is the epidermis that primarily performs the barrier function of the skin.

Within the external layer, i.e. the epidermis (upper skin), the stratum corneum has special significance. As per a skin model developed by Elias the structure of the corneal layer is similar to a red brick wall (bricks and mortar model). In this model the corneocytes correspond to the bricks and the lipid membrane in the intercellular space represent the mortar. The dead horny cells (corneocytes) constantly scale off on the outside resulting in the corneal layer to be constantly renewed.

Generally speaking, the corneal layer is an effective barrier against the invasion of foreign substances, bacteria, viruses and the like. On the other hand, with respect to the transdermal transport of drugs the barrier function of this skin layer proves to be obstructive. Customary cosmetic and pharmaceutical preparations are hardly ever capable of overcoming this epidermis barrier so that a penetration of the relevant active compounds is very rarely accomplished.

More often than not, undesirable side effects are encountered when medications are administered systemically. Especially when anti-inflammatory (antiphlogistics) and pain-killing drugs (analgesics) etc. are administered via the gastrointestinal tract it is not infrequent that serious complications are experienced. Forms of administration circumventing the stomach and intestine tract are injections, infusions etc., which necessitates that body tissue has to be injured (punctured), or injury-free methods such as transdermal plasters, sublingual medication and the like the absorption rate of which is low.

For these reasons, a topical administration of drugs through the skin though meaningful and expedient is nevertheless difficult to perform hitherto due to the barrier function of the outer skin.

Various methods are known to overcome the skin barrier, inter glia electroporation, electrophoresis, sonophoresis, transdermal plasters or jet injections. However, these methods are merely capable of transporting dissolved active agents through the skin, whereas supplying the skin with oxygen is not possible or has not yet been attempted.

From a therapeutic viewpoint, the success of a transepidermal administration of active compounds in the interest of achieving local effects is dependent on whether an optimum concentration-time profile of the active compound in the skin can be accomplished. This process is decisively governed by the structural and functional changes of the treated skin.

Penetration denotes the ingress of active agents into the skin; usually this refers to an ingress into the upper skin. Permeation on the other hand denotes an intake of substances passing through the epidermis to such an extent that a systemic resorption can take place by absorption in the blood vessel system of the dermis. In medical terminology adjectives describing a permeation are transdermal or percutaneous, while in the cosmetic field also a penetration into the epidermis is referred to in this way. Therefore, these terms are not unambiguous. For that reason, the term transepidermal is used in the following to describe a permeation of the skin surface extending into the dermis.

In the cosmetic field spray systems via which preparations are applied onto the skin are known, commonly used, and widely spread. The barrier function of the skin prevents, however, a transepidermal transport.

Hypoxia is a pathological condition of the body as a whole (generalized hypoxia) or of a body region (tissue hypoxia) caused by an insufficient supply of molecular oxygen. A cellular incongruity between the supply of oxygen and the oxygen requirement results in hypoxia. As a result of this, a diminished production of energy occurs in the mitochondria. These circumstances may damage the cells causing an inflammatory reaction of the affected tissue.

A prolonged, chronic hypoxia is responsible for the manifestation of a variety of diseases (rheumatic and cardiovascular diseases, chronic wounds, impairment of intellectual capacity, diabetic sequelae etc.). On the other hand, a reactive inflammation may also lead to local hypoxia due to increased metabolic activity.

Hypoxia could be alleviated or compensated when hypoxic cells and organs are therapeutically supplied with oxygen. Moreover, also an enhanced perfusion (achieved, for example, by medical treatment) improves the oxygen supply situation.

Customary oxygen therapies are based on inhalation, i.e. they are systemic administrations. Other forms of oxygen therapy are known from the state of the art, for example the administration of gaseous oxygen, the hyperbaric oxygen therapy (HBO), the use of artificial blood from perfluorocarbons, or the oxygenation for wound treatment purposes, although the oxygen is not applied via the skin in this case. Aside from this, cosmetic preparations are known which contain oxygen (WO 2005/016309 A1 or WO 2006/094550 A1) as well as spraying systems by means of which an oxygen-enriched liquid is to be sprayed on the skin and wherein the overpressure needed to bring the active agents into the skin only being produced subsequently (US 2005/0228338 A1), while the amount of oxygen capable of penetrating into the skin when employing this method is very small, however. Moreover, only a small skin area can be treated in each case. At the present time, no method is available by means of which oxygen in sufficient quantity can be applied through the outer skin into deeper skin layers.

It is of great therapeutic significance to find a method that enables active agents and oxygen to simultaneously pass through the skin. In case of a local treatment, it is desirable to apply the medication and the oxygen directly at the treatment site so that undesirable systemic side effects of the active compounds are minimized.

Publication WO 2006/040119 A2 describes a method, but does not provide further proof in this respect, according to which the introduction of oxygen into the corneal layer and thus an increase of the partial oxygen pressure on the tissue side of the stratum corneum shall result in an improvement of the transdermal transport of the medication applied. In this context, the medication was administered in the form of microemuisions. As medication substances both natural and artificial active agents of various kind were named aimed at covering a variety of indications. The microemulsion was to be applied with the help of an application system comprising a device for the atomization of the microemulsion by means of a gas, in particular oxygen. The application in this respect was restricted, however, to microemulsions and comparatively minute active agent molecules.

Proceeding from what is known from prior art it is therefore the objective of the invention to provide an application system for the percutaneous administration of medication by means of which the active agents can be introduced in an even more effective manner into large areas of the skin, and without causing skin injury.

As proposed by the invention this objective is accomplished by an application system for the transepidermal surface administration of pharmaceutical or cosmetic active agents, said system comprising a container accommodating a sprayable, active agent-containing composition, a propellant gas source for pressurized gas consisting of at least 25% v/v of oxygen, and a spraying device, wherein container, propellant gas source, and spraying device are flow-connected with each other in such a manner that the propellant gas atomizes the sprayable composition and forces it out of the spraying device when the spraying device is actuated, and wherein the composition is forced out of the spraying device in the form of a conical spray jet at an exit velocity of ≥100 m/s.

Surprisingly, it has been found that the application of active compounds via the skin can be substantially improved if the exit velocity of the carrier gas stream conveying the atomized active agent composition is increased to more than 100 m/s. If appropriate nozzles are employed as spraying device even larger molecules can be introduced through the skin. It is not imperative that the active agent composition is provided in the form of a microemulsion although microemulsions are preferred in view of the dissolution of oxygen, because due to the increase in exit velocity emulsions, nanoemulsions, gels, liposomes, microbubbles, microfoams, and other sprayable compositions may be administered as well.

Another surprising effect that could be observed when using a nozzle having a high exit velocity, especially a de Laval nozzle, was that significantly greater amounts of oxygen could dissolve in the vehicle (i.e. the sprayable composition). This makes it possible to introduce significant amounts of oxygen into the skin in addition to the active compounds. In this manner a local hypoxia, e.g. of inflammatory nature, can be treated and the effect of the administered active agents intensified synergistically.

Although nozzles that enable an exit velocity of more than 100 m/s to be reached are also known in the jet technology field which provides for a liquid to be accelerated momentarily (explosively) to high velocities either mechanically or also with the aid of a propellant gas, this technology nevertheless requires the skin to be penetrated by a sharp jet and thus injured. Essentially, the jet technology is just to be considered an alternative to customary injections for which needles are employed. For that reason, the jet technology is primarily used for systemic administrations, for example vaccination purposes.

In contrast to this the inventive system provides for the active agent composition to be continuously applied to large areas and over a longer time period of several minutes. The exiting spray jet has a conical shape. Moving the discharge nozzle enables large skin areas to be treated. A treatment may take place over a longer time span of between 10 and 30 minutes. The discharge angle of the spraying device, i.e. the opening angle of the spray jet cone, should be at least 10°, preferably at least 15°, especially preferred at least 20°. Typical angles range between 15° and 30°. However, conceivable are even greater discharge angles to enable a large area to be sprayed without having to move the spraying device itself, but for practical reasons the discharge angle as a rule shall not be greater than 45° or 60°. Nevertheless, large skin areas can also be sprayed with a smaller spray jet angle due to movements the spraying device can perform. The spray-covered surface as a rule ranges between 10 and 100 cm$^2$, but may even be considerably greater, especially when veterinary medical applications are concerned. During the process, the skin is neither injured nor stressed in any other way but solely the enrichment of oxygen beneath the skin enables the barrier function of the skin to be overcome temporarily and allows active agents to be transdermally transported.

The relationship between length and diameter of the discharge of the spray device has an influence on the composition of the spray jet. A relatively short discharge element tends to produce a larger jet cone angle (discharge angle) than a discharge element which is longer in the direction of flow. This leads to a greater surface the spray jet can cover with the jet penetration depth decreasing simultaneously, however.

The invention differs from the known jet technology not only in that the active agent composition to be applied is intended to cover large areas of the skin but also in that oxygen is employed as propellant gas. For purposes of the jet technology other inert gases (nitrogen, carbon dioxide, argon) are used while the administration of oxygen through the skin does not play a role in this context.

Oxygen used in the application system according to the invention not only functions as carrier gas but is also applied to perform the function as another "active agent". Surprisingly, it has become evident that in the treatment of a variety of diseases a synergistic effect emerged through interaction of the active agent proper and the oxygen. Hypoxic tissue, i.e. tissue having a reduced oxygen content, is associated with a number of illnesses. An inadequate supply of oxygen is caused in particular by the blood flow through tissue being insufficient (impaired microcirculation) or through the $O_2$ bonding capacity of hemoglobin being too low. Diseases which are associated with a hypoxic condition are, for example, rheumatism or psoriasis.

Through the use of another spraying device having an exit velocity of at least 100 m/s the size of the droplets applied to the skin is distinctly reduced in comparison to what has been proposed by WO 20061040119 A2 which is to be deemed advantageous in terms of skin penetration. Using the inventive application system enables droplets with a diameter of less than 100 nm to be produced. The droplets are capable of deeply penetrating into the skin to approx. 30 to 150 µm.

The discharge opening may be located 10 to 30 mm away from the skin; this is the distance up to which an effect can be demonstrated. Typically, the distance is only 10 to 20 mm, however, and does not exceed 1 cm. The jet width at the discharge opening amounts to 4 to 6 mm, with the jet propagating in a conical fashion from the discharge opening. The opening of the spraying device is slowly passed over the skin area to be treated. Basically however, the speed at which the nozzle opening is moved is negligible.

The exit velocity of the spray jet preferably amounts to at least 300 m/s, in particular 300 to 400 m/s. It has been determined that at such a jet velocity the application of the active agent through the skin is most effective. This is also true if comparatively large molecules are to be administered as active agents.

The spraying device is preferably provided in the form of a de Laval nozzle. In a de Laval nozzle the cross sectional area is initially constricted and towards the discharge opening widens again so that a fluid passing through the nozzles can be accelerated to supersonic speed at the point of the narrowest cross section of the nozzle. Using such a nozzle thus enables the desired high discharge velocities to be attained.

The propellant is oxygen or an oxygen-rich gas mixture containing at least 25% v/v, preferably at least 60% v/v of oxygen. In most cases almost pure oxygen is used having a content of at least 98% of oxygen.

However, aside from oxygen the propellant may also contain other gases or other gases may be added to the propellant. These may just be minor impurities but other gas types that enable additional effects to be produced may be employed as well. An example of the admixture of a gas is the use of nitrous oxide $N_2O$.

The gage pressure produced by the propellant typically ranges between 1 and 7 bar, preferably between 2 and 4 bar, especially preferred amounts to approx. 3 bar. In this way, a sufficiently high oxygen enrichment can be accomplished both in the composition and subsequently in the dermis. At elevated pressure a microemulsion is capable of dissolving significant amounts of oxygen; at a pressure >5 bar, for example, 10 to 100 times more than at atmospheric pressure. The depth of penetration into the skin typically ranges between 30 and 150 μm.

Preferably and if so required, the application system is capable of introducing onto the skin the propellant gas only, i.e. oxygen or an oxygen-rich gas mixture without the composition. It may often be found expedient to initially spray the composition on the skin and then proceed with applying pure oxygen for a time span of several minutes with a view to further improving the absorption of the active agent and oxygen through the skin.

A microemulsion is especially preferred as sprayable composition. The special properties of microemulsions are closely related to their colloid-chemical structure. Microemulsions may be viewed or described as “critical solutions”. Such systems possess properties known both from emulsions (particulate) and from solutions (no interfacial surface tension between oil and water components, thermodynamic stability). Microemulsions are emulsions wherein the dispersed phase forms particularly minute droplets resulting in light not being scattered. Other than customary emulsions microemulsions therefore are clear, do not exhibit a milky haze and, moreover, are permanently stable. Aside from the oil and water phase a microemulsion contains a tensile and a co-tensile. Considering all these properties as a whole makes microemulsions very interesting as carrier system for active compounds in the field of pharmaceuticals and cosmetics.

Preferably, the mean droplet size of the sprayed composition is less than 300 nm, preferably less than 150 nm, and further preferred less than 100 nm. It has surprisingly been found that a microemulsion at elevated pressure is capable of dissolving significant amounts of oxygen; at a pressure >5 bar, for example, 500 to 1000 times more than at atmospheric pressure. The amount of oxygen dissolved in the microemulsion typically ranges between 0.3 and 0.8 ml $O_2$/ml of microemulsion (at 25° C., 3 bar, 25 l/min); this is 4 to 10 times more than stated in publication WO 2006/040119 A2.

However, by using a spraying device operating at a very high exit velocity other compositions can be applied as well, for example customary emulsions, nanoemulsions, gels, microfoams, suspensions and compositions containing liposomes or microbubbles. In principle, any solution containing a dissolved active agent or optional types of dispersions can also be administered.

Typically, the application system contains a supply of sprayable composition amounting to between 0.2 and 10 ml. During application the volume flow of sprayable composition typically ranges between 0.1 and 10 ml/min., preferably between 0.3 and 5 ml/min, and especially preferred between 0.5 and 2 ml/min. During each application cycle relatively great volumes of at least 1 ml are thus applied to the skin as a rule because of which the inventive application system is different from the jet technology mostly used for vaccination purposes during which only small volumes of up to approx. 0.5 ml are introduced into the skin. Typically, up to 2 ml of the preparation are sprayed onto 100 $cm^2$ of skin surface. Usually, the spray application of the composition is followed by additionally spraying an oxygen-rich propellant gas on the skin.

The amount of propellant discharged from the application system per minute via the exit opening typically ranges between 10 and 100 l, preferably between 15 and 50 l, and especially preferred between 20 and 30 l. However, the discharge rate in liters depends on the pressure applied. Depending on the discharge rate in liters and the available supply of propellant gas operating times of between 20 and 60 min. are thus achievable.

Apparatus of various kind are suitable as propellant gas source, for example an oxygen cylinder or an oxygen generator. The application system can also be connected to a line via which oxygen is supplied continuously so that the system may be operated nearly without interruption.

Another possibility to improve skin penetration is to further reduce the applied droplets in size. For this purpose a small turbine wheel can be arranged downstream of the spraying device viewed in the discharge direction of the jet. This turbine wheel is set in motion through the jet itself. The turbine wheel may as well be driven additionally from the outside. Due to the fact that the jet has to pass through the rotating turbine wheel it is additionally “chopped up” resulting in the droplets that hit the skin to be of a very minute size and also enable a larger skin area to be sprayed.

As per another advantageous embodiment the application system is provided with means for a temporary interruption of the spray jet being discharged from the spraying device. The interruption should be adjusted such that the spray jet is interrupted at least once but preferably several times per second. The spray jet may, for example, be interrupted 6 to 14 times, preferably 8 to 12 times, especially preferred approx. 10 times per second. The interruption may be brought about for example by means of a turbine wheel by means of which the spray jet is “chopped up”, Nevertheless, other technical solutions may be resorted to as well to bring about a ‘clocking’ of the spray jet by subjecting it to brief short-time interruptions. To this end other mechanical obstructions are conceivable, for instance, which are briefly introduced into the spray jet. Also conceivable is the use of quick-opening valves controlling the flow of the gas arriving from the propellant gas source. Such valves may, for example, be of oscillating or electromagnetically controlled type.

Surprisingly, it has been found in this context that interrupting the spray jet temporarily not only enables the gas consumption to be reduced but also improves the skin penetration effect, i.e. the same amount of the sprayed composition is absorbed within a shorter period of time without the skin becoming oversaturated. The reason for this surprising effect could not be exactly determined; it is felt that due to the interruption of the spray jet the kinetic energy of the individual droplets increases as a result of the back pressure arising when the flow is interrupted. It may also be possible that due to the cycled interruption of the spray jet a physical stimulation of the skin takes place resulting in an improved absorption behavior. The combination of higher forces exerted (back pressure and acceleration moment) and skin stimulation probably causes the absorption capacity of the skin to increase significantly.

Typical medical indications where the inventive application system can be employed are skin diseases with viral, bacterial, and fungal infections, skin cancer, psoriasis, atopic dermatitis, inflammatory skin (diabetes, chronic-venous insufficiency (CVO), and other inflammations, wound healing, inflammatory-rheumatic diseases, pain relief/analgesia and periodontitis. Moreover, the application system can also be used to perform cosmetically relevant treatment (cellulite, vitiligo, anti-aging, etc.).

In addition to the inventive application system the invention also relates to an appropriate method.

Figure 1:
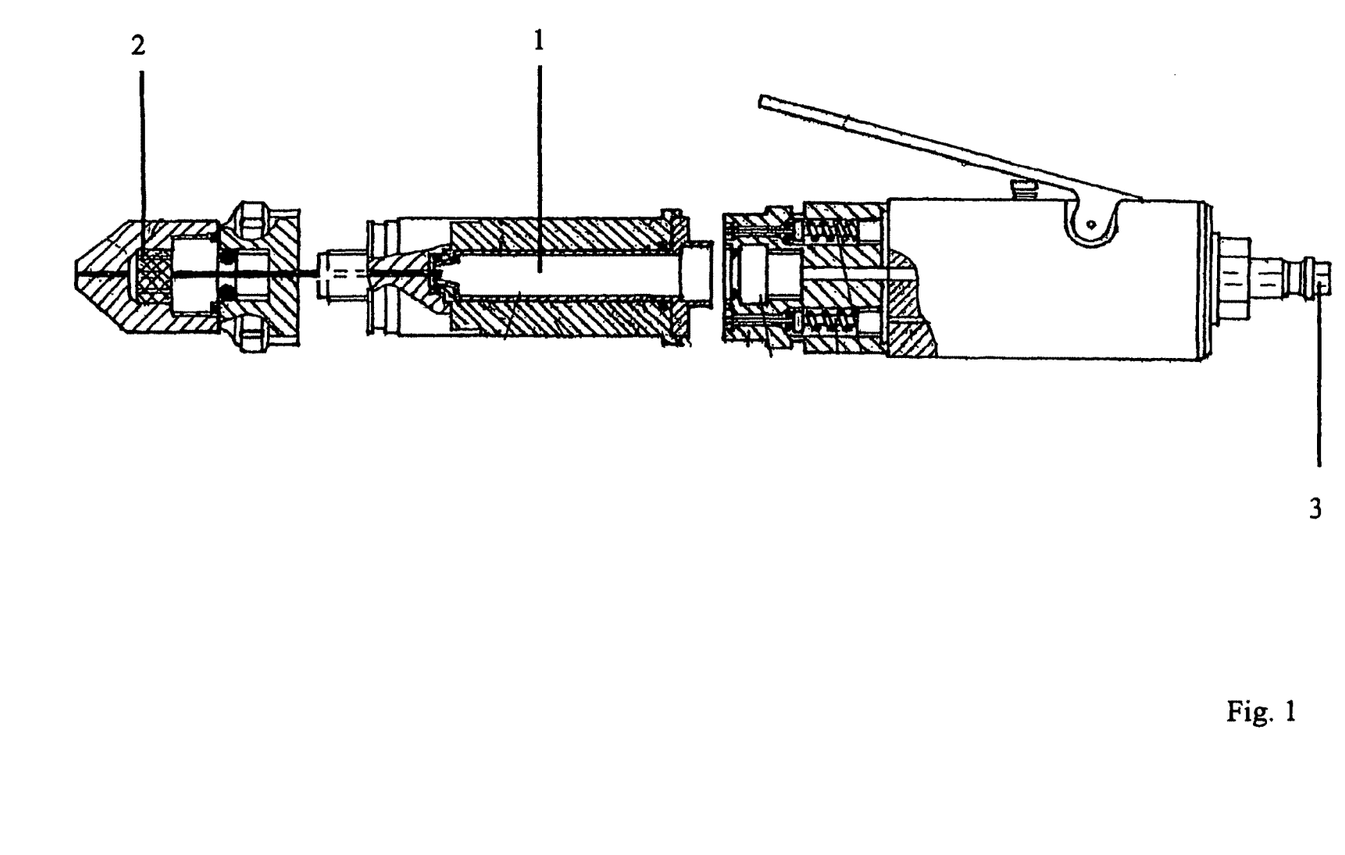

FIG. 1 shows the essential components of the application system in accordance with the invention. The system is provided with a container 1 accommodating the active agent-containing sprayable composition as well as a propellant gas source 3, in the present case in the form of an oxygen feed system via an external line. Upon actuation of the application system the propellant gas forces the sprayable composition through the spraying device 1, which is a de Laval nozzle. For this purpose, container 1, propellant gas source 3, and spraying device 2 have been appropriately flow-connected with each other.

Figure 2:
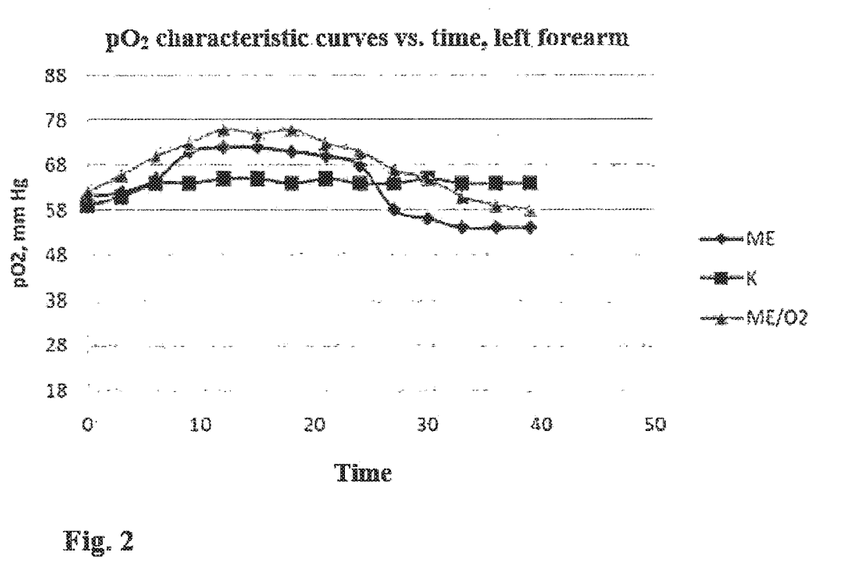

FIG. 2 shows $pO_2$ characteristic curves vs. time for a female test person M. K., 27 years old, left forearm.

The present invention is elucidated in more detail by way of examples.

EXAMPLE 1

Pain Relief through Application of a Lidocaine-Containing Microemulsion with Additional Oxygenation The effect of a pain alleviating 5% lidocaine-containing microemulsion (ME-Lido) was investigated on 18 voluntary test persons (8 male and 10 female, aged between 23 and 45 years). The ME-Lido preparation was tested versus the EMLA® cream (AstraZeneca). Approx. 2 g of EMLA® cream were applied to 10 cm² of skin (forearm). To approx. 30 cm² of skin area on the forearm the ME-Lido microemulsion was applied by means of the inventive application system (2 bar, 15 l/min) over a period of 60 to 75 seconds and oxygen was subsequently sprayed on the area for 10 minutes. After different exposure periods the sensation of pain was checked through little pinpricks. The participating persons assessed their pain sensation on a pain intensity scale (0—no pain, 5—normal pain and 10—intense pain).

TABLE 1

Time vs. analgesic potential of the EMLA ® cream und the lidocaine-containing microemulsion applied with the inventive application system.

| Vehicle | Time/minutes | Pain intensity |
|---|---|---|
| ME-Lido with $O_2$-spraying | 15 | 7.5 |
|  | 30 | 5.3 |
|  | 45 | 3.0 |
|  | 60 | 2.0 |
|  | 120 | 2.2 |
|  | 180 | 3.0 |
| EMLA ® cream | 15 | 9.5 |
|  | 30 | 9.0 |
|  | 45 | 6.0 |
|  | 60 | 3.0 |

The inventive method shows a moderate analgesic effect before 30 minutes had elapsed and effective analgesia was achieved after 45 minutes with a lasting effect of at least 3 hours, whereas it takes 1 hour for EM LA cream to have any effect.

EXAMPLE 2

Antirheumatic Effect

Patients Suffering from Rheumatoid Arthritis were Treated.

All treatments were carried out by applying microemulsions containing diclofenac (5%) and curcumin (2%). The microemulsion in an amount of 0.5 to 0.7 ml was applied to the affected area by means of the inventive application system and then gently massaged into the skin. Afterwards, the affected area was additionally treated with oxygen for a period of 20 min. Treatment was as a rule carried out twice or three times a week. Success of the treatment was determined with the aid of the visual analog scale (VAS) and rated as a decrease in the relevant pain. The treatment duration ranged between 1 month and 3 months depending on the success of the treatment.

TABLE 2

Indications, number of cases and treatment success

| Indication | Number of patients | Success | No success |
|---|---|---|---|
| Arthrosis of upper subtalar joint | 7 | 6 | 1 |
| Arthritis of knee joint | 7 | 6 | 1 |
| Arthritis of the hip | 7 | 6 | 1 |
| Total | 21 | 18 | 3 |

As can be seen from the table the treatment success was 85.7%.

EXAMPLE 3

Therapy of Horses Suffering from Inflammatory Diseases

Treatment was carried out by applying a boswellic acid (2%) and a curcumin-(2%)-containing microemulsion. The microemulsion in an amount of 0.5 to 1.0 ml was applied to the affected area by means of the inventive application system. Afterwards, the affected area was additionally treated with oxygen for a period of 20 min. Treatment was as a rule carried out twice or three times a week.

TABLE 3

Therapy of 15 horses suffering from inflammatory diseases

| Indication | Disease cases | Treatment successful | Treatment not successful |
|---|---|---|---|
| Coffin joint inflammation | 7 | 6 | 1 |
| Fetlock joint inflammation | 8 | 7 | 1 |
| Total | 15 | 13 (87%) | 2 (13%) |

As can be seen from the table the treatment success was 87%.

EXAMPLE 4

Treatment of Cellulite

For the treatment of female test subjects 0.7 ml of circulation-stimulating microemulsion (with methyl nicotinate (1.0%), ethyl salicylate (2.0%) and carnitine (1.0%)) was applied with the aid of an application system. Treatment was carried out at an oxygen pressure of 3 bar and a consumption of 25 l of $O_2$/minute for a period of 15 minutes on the selected skin area. Under these conditions the skin was additionally massaged with oxygen.

28 female subjects took part in a three to five-week treatment course. Treatment was carried out three times a week and focused on a selected area of one thigh. The opposite side was left untreated and served control purposes. The test subjects were divided into two groups. Those in one group were treated with the microemulsion while the female test subject in the other group were treated with microemulsion plus oxygen.

Elasticity of the skin was measure by means of a cutometer (DermaLab-System, Cortex Technology, Denmark). This process enables the skin elasticity to be determined down to a depth of 1.5 mm.

Each value is the mean of three measured values taken at three different neighboring places of the skin area.

TABLE 4

Relative increase in skin elasticity ($\Delta E/E_0$) after treatment periods of 3 and 5 weeks in comparison to untreated skin areas.

| Treatment time | Treatment | Skin elasticity, $\Delta E/E_0$, % |
|---|---|---|
| | Microemulsion (group 1) | |
| 3 weeks | without treatment | 0.2 ± 0.40 |
| | with treatment | 30.1 ± 2.14 |
| | Microemulsion plus oxygen (group 2) | |
| | without treatment | 0.8 ± 0.35 |
| | with treatment | 35.6 ± 2.35 |
| | Microemulsion (group 1) | |
| 5 weeks | without treatment | 0.4 ± 0.33 |
| | with treatment | 41.6 ± 3.16 |
| | Microemulsion plus oxygen (group 2) | |
| | without treatment | 0.6 ± 0.45 |
| | with treatment | 52.3 ± 3.36 |

After 5 weeks of treatment the skin elasticity was found to have increased in group 1 (microemulsion) by approx. 41% and in group 2 (microemulsion plus oxygen) by 52%. The treatment with oxygen enables an increase in skin elasticity to be achieved by approx. 10% in comparison to a treatment in the absence of oxygen.

EXAMPLE 5

Treatment of Chronic Periodontitis

In the framework of a multicentric study 28 patients (aged 48±3 years on average) suffering from chronic periodontitis were examined. The treatment started with an initial therapy comprising a minimum of two professional tooth cleaning operations during which plaque and dental calculus was removed manually and mechanically. The examinations necessary for this study were carried out by certified dentists. Using a periodontal probe (WHO DB 767) the probing depths (ST) and the attachment levels (AL) were determined.

One day after the last tooth cleaning operation the adjuvant therapy was performed with the aid of an inventive application system with the vehicle (an OM/microemulsion containing 2% chitooligosaccharides, 0.2% curcumin and 0.5% ethyl salicylate). Oxygenation was carried out at p=1.7 bar and a consumption of 10 l/min in the course of 10 minutes.

In the clinical study 8 persons without adjuvant therapy (control group), 10 patients with microemulsion (group 1) and 10 patients with microemulsion plus oxygenation (group 2) were treated. The clinical parameters (ST, AL) were determined prior to the start of the therapy as well as 2 and 4 months thereafter.

The average values of all patients at the time of the baseline examinations were found to be in the pathological range (ST≥3.5 mm and AL≥4.3 mm).

TABLE 5.1

Reduction of the ST values ($p \leq 0.001$)

| | Probing depth/mm | | | | |
|---|---|---|---|---|---|
| Patients | Baseline | 2 months | Difference | 4 months | Difference |
| Control | 3.98 ± 0.36 | 2.78 ± 0.35 | 1.2 | 2.72 ± 0.32 | 1.26 |
| Microemulsion | 3.96 ± 0.53 | 2.64 ± 0.37 | 1.32 | 2.56 ± 0.27 | 1.40 |
| Microemulsion plus $O_2$ | 4.03 ± 0.68 | 2.45 ± 0.40 | 1.58 | 2.23 ± 0.39 | 1.80 |

The maximum reduction took place during the first two months after the therapy. In the following two months only marginal differences were determined within a group for the ST values.

When comparing the individual groups a pronounced probing depth reduction (1.80 mm after 4 months) was achieved in group 2 (microemulsion plus $O_2$). In group 1 (microemulsion) the values were found to be slightly lower, i.e. 1.40 mm after 4 months, but were still significantly different from the values established for the control group,

TABLE 5.2

Reduction of the AL values ($p \leq 0.001$)

| | Attachment level/mm | | | | |
|---|---|---|---|---|---|
| Patients | Baseline | 2 months | Difference | 4 months | Difference |
| Control | 4.36 ± 0.36 | 3.75 ± 0.35 | 0.61 | 3.60 ± 0.32 | 0.76 |
| Microemulsion | 4.27 ± 0.53 | 3.15 ± 0.37 | 1.12 | 3.06 ± 0.27 | 1.27 |

TABLE 5.2-continued

Reduction of the AL values (p ≤ 0.001)

| | Attachment level/mm | | | | |
|---|---|---|---|---|---|
| Patients | Baseline | 2 months | Difference | 4 months | Difference |
| Microemulsion plus $O_2$ | 4.62 ± 0.68 | 3.11 ± 0.40 | 1.51 | 2.61 ± 0.39 | 2.01 |

At any time after the therapy the highest attachment gain was determined in group 2. Two months after the therapy it amounted to 1.51 mm, 4 months later it was found to be 2.00 mm. In the therapy where microemulsion was used (group 1) the values were lower (1.12 mm after 2 months, 1.27 mm after 4 months). The lowest attachment gain was found in the control group. The attachment gain by 0.74 mm (after 4 months) found between the microemulsion group and the group with the additional oxygenation treatment suggests that there is a synergistic effect between microemulsion and oxygen.

EXAMPLE 6

Evidence of Skin Penetration by Means of Fluorescein

Immediately after slaughtering, pig ears without skin injuries were picked up from a slaughterhouse. The ears were thoroughly washed with mild soap. Immediately afterwards, the subcutaneous layer of fat was removed using a scalpel. The skin was stored in a container at −20° C. for further examination. Separating the epidermis from the dermis was carefully carried out after heating at 60° C. (1 minute).

The penetration tests were carried out with the help of a Franz diffusion cell which had an effective diffusion area of 0.636 cm² (SES-Analysensysteme, Germany).

0.5 ml of microemulsion containing 0.3 mg/ml of fluorescein was introduced into the donor compartment of the cell by means of the inventive system (2.0 bar, V=15.0 l $O_2$/min). Following this, oxygenation took place for a period of 15 minutes. An isotonic PBS solution was used as acceptor fluid.

After 3 hours the skin was taken out and fixed in a 4% formalin solution, embedded in paraffin, cut into 5 µm thick slices and frozen at −70° C.

The skin samples were examined histologically. The intensity of the fluorescence was investigated for each sample by means of a confocal laser scanning microscope (Zeiss) at 10-times magnification.

Two regions (each 900 pixel) of the dermis and of the epidermis were selected and the intensity relationship situation in these regions assessed by computation. From the histogram generated intensity values higher than 150 pixel were taken.

TABLE 6

Fluorescence relationship dermis to epidermis

| Preparation | Relationship of Fluorescence in Dermis/Epidermis |
|---|---|
| Fluorescein in water | n.d. |
| Microemulsion with fluorescein | 0.8 |
| Microemulsion with fluorescein plus $O_2$ treatment | 1.3 |

As is evident, the oxygen spraying apparatus according to the invention enables a significantly improved penetration into the deeper skin layers so that active ingredients can act more effectively.

EXAMPLE 7

Increasing the Transcutaneous Oxygen Partial Pressure ($pO_2$) by Means of a Microemmulsion and Oxygen The transcutaneous oxygen partial pressure measurement is a non-invasive polarographic method for the indirect determination of the oxygen partial pressure ($pO_2$) at the skin surface (to a depth of 200 µm) and an indirect measurement of the systemic arterial $pO_2$. Proof of oxygen penetration into the skin was determined by means of TCM 4 (Radiometer, Denmark) by measuring the transcutaneous oxygen partial pressure.

The measurements were taken on healthy test persons who had no skin injuries/diseases. During the measurement period the test persons were not permitted to consume coffee, cigarettes and alcohol. The measurements were taken in an air-conditioned room (T=20-23° C.).

Hair was shaved off and the skin first cleaned with a cleaning agent (Bacillol® 25, Bode Chemie, Germany) and dried in the air. Adhesive rings for three electrodes were attached to the inside of the forearm 3 cm away from the elbow (No. 1: control), 6 cm away from the elbow (No, 2: microemulsion) and to a site between the above two spots slightly below their connecting line (No. 3: microemulsion administered through the inventive application system with oxygen). The examined preparation (0.2 ml O/W microemulsion) was introduced into adhesive ring No. 2 and rubbed in gently and applied to adhesive ring No. 3 by means of the system in accordance with the invention. After 10 minutes exposure (with/without oxygenation) the remainder of the microemulsion was carefully removed with a cloth. Electrolyte solution (Radiometer, Denmark) was applied to all adhesive rings and the electrodes were attached. The measurements were taken at 37° C. and 45° C. but not before stable values had been reached (after approx. 10 minutes).

Skin treated with the microemulsion—both with and without oxygenation—showed already after 7 minutes higher $pO_2$ skin values in comparison with the control measurements. These values increased further and reached their maximum after approx. 15 to 20 minutes ($pO_2$ value of the microemulsion increased by 10% and $pO_2$ value of microemulsion plus oxygen by 20% in comparison with control measurements). The fact that after approx. 30 minutes the $pO_2$ values for microemulsion and microemulsion plus oxygen decreased more than found by control measurements is indicative of an increased oxygen consumption in the skin cells.

The peeled skin showed a $tcpO_2$ value of approx. 95 mm Hg which is roughly 32% higher than found by control measurements. This attests to the fact that the stratum corneum is an effective barrier impeding oxygen penetration through the skin. The inventive method enables this barrier to be overcome to a significant extent.

EXAMPLE 8

Clinical Study of a Psoriasis Therapy with Methotrexate Microemulsion with and without Application of Oxygen (Synergistic Effect)

To obtain evidence of the positive effects for the treatment of psoriasis through the administration of methotrexate and the use of the inventive application system aimed at healing up psoriasis, a multicentered placebo-controlled parallel group study was carried out involving 30 patients diagnosed with plaque-type psoriasis. The patient group (male/female) was randomly distributed and contained 10 patients each. The treatment continued over a period of 14 weeks with three treatments per week. The placebo group was given a placebo microemulsion without methotrexate. The microemulsions were applied to the skin directly (placebo group and methotrexate group) and with the help of the inventive application system (methotrexate plus oxygen group).

Inclusion Criteria:
The most important inclusion criteria were as follows:
Long-term plaque-type psoriasis
Disease duration at least 36 months
Severity of sporadic changes in the skin were judged as slight (42.0%) and medium (58%).
Not more than 25% of the body surface should have been affected.

The most important exclusion criterion was: Patients that had received a systemic or UV therapy less than 2 months ago.

The extent and seventy of the skin changes were assessed with the help of the Psoriasis and Severity Index (PASI). Erythema, induration, and scaling of body portions were evaluated. For general assessment a scale of 0 to 5, from completely clear to not healed.

Both the clinical symptoms and the statements made by the patients were documented. Moreover, biochemical analyses were performed on a regular basis.

The effectiveness of the therapy given was determined by measuring the PASI values.

Student's t-test was used for the evaluation of measured values. The results were determined as p-value. With a significance level p=0.05 a result is deemed as statistically significant.

TABLE 7

PASI value improvement vs. therapy duration

| Therapy duration | Placebo | Active treatment | |
|---|---|---|---|
| Week | ME | MTX | MTX plus oxygen |
| 2 | 6.81 ± 0.22 | 5.2 ± 0.24 | 4.1 ± 0.26 |
| 4 | 6.78 ± 0.24 | 4.8 ± 0.31 | 3.0 ± 0.31 |
| 6 | 6.72 ± 0.32 | 4.2 ± 0.27 | 2.8 ± 0.25 |
| 8 | 6.53 ± 0.27 | 3.4 ± 0.25 | 2.4 ± 0.22 |
| 10 | 6.46 ± 0.31 | 3.2 ± 0.22 | 2.0 ± 0.32 |
| 12 | 6.37 ± 0.35 | 2.6 ± 0.27 | 1.7 ± 0.30 |
| 14 | 6.25 ± 0.32 | 2.4 ± 0.23 | 1.5 ± 0.26 |

ME: Microemulsion w/o methotrexate;
MTX: Microemulsion with 0.25% w/w of methotrexate After 15 weeks of treatment a complete healing of the psoriatic target areas was observed in 16 patients (80%).

By the biochemical analyses that were carried out (blood: Hb, RBCS, urea; Liver. SGOT, SGPT, alkaline phosphatase; Kidney: Creatinin, urea) no negative effects could be detected. The preparations appeared to be well tolerated. Only 3 patients reported a mild, temporary, burning sensation that was felt at the beginning of the treatment (in the 2nd week).

Synergistic Effect.

The additional administration via the inventive application system and the treatment with oxygen (MTX plus oxygen) have positive effects on the healing process. After 6 weeks the PASI values had improved by 37% (MTX group) and 58% (MTX plus oxygen). After 14 weeks the PASI values had improved by 64% (MTX group) and 88% (MTX plus oxygen).

EXAMPLE 9

Examination of the Penetration Behavior of a Curcumin-containing Microemulsion with and without Spray Jet Interruptions The penetration behavior of a curcumin-containing microemulsion (2%) was tested on 13 voluntary test persons (8 male, 5 female, aged between 26 and 52 years). The curcumin-microemulsion was applied to approx. 25 cm$^2$ of skin (5×5 cm area on forearm) by means of the inventive application system (2 bar, 15 l/min). A comparison area of identical size located on the opposite forearm was in each case selected to which curcumin-microemulsion was also applied by means of the inventive application system (also at 2 bar and 15 l/min) but in this case combined with the inventive interval clocking system (interruption of the spray jet at a frequency of 10 Hz, corresponding to 10 interruptions per second is and thus producing higher kinetic energy in the non-interrupted interval).

Both comparison areas were treated at a velocity of 1 cm/s and a distance of 1.5 cm away from the skin of the patient by arranging alternately five parallel lines each in longitudinal direction and five parallel lines transversely until a visible oil film had formed on the skin. In both areas the application system according to the invention dispensed 0.0012 ml/s each.

Whereas in the area treated without the spray jet being interrupted the skin saturation (formation of an oil film) occurred after approx. 185 seconds on average (corresponding to 0.22 ml of curcumin-microemulsion), an oil film in the area treated with jet interruptions only occurred after approx. 245 seconds on average (corresponding to 0.29 ml of curcumin-microemulsion). This corresponds to an average increase of the absorption capacity of the skin due to the jet interruption feature by 34%.

Subsequently, the patients were treated in a third adjacent comparison area also sized 5×5 cm (on forearm) again with curcumin-microemulsion via the inventive application system, on one arm without and on the other with jet interruption cycles; in this case, however, with the dispensing speed of the application system raised by 34% (to 0.0016 ml/s). All other parameters remained unchanged. Treatment again took place by producing a 5×5 grid in cross-wise fashion with the time being determined until an oil film formed on the skin (saturation).

In the area treated with jet interruption cycles being applied 177 seconds on average elapsed until saturation was reached, corresponding to 0.285 ml which is nearly the amount previously administered at lower speed and nearly the time that led to saturation with 0.22 ml at previously lower application speed and without jet interruption cycles being provided.

In the area treated without interruption cycles at an application speed increased by 34% saturation now occurred after 124 seconds on average (corresponding to 0.2 ml),

TABLE 8

Time until skin saturation was reached (oil film formation)

| Patient | V = 0.0012 ml/s | | V = 0.0016 ml/s | |
|---|---|---|---|---|
| | w/o interruptions | with interruptions | w/o interruptions | with interruptions |
| 1 | 180 | 239 | 122 | 177 |
| 2 | 194 | 253 | 129 | 183 |
| 3 | 152 | 203 | 100 | 145 |
| 4 | 168 | 221 | 115 | 159 |
| 5 | 202 | 269 | 136 | 193 |
| 6 | 197 | 258 | 130 | 183 |
| 7 | 184 | 241 | 126 | 180 |
| 8 | 179 | 239 | 121 | 171 |
| 9 | 193 | 257 | 127 | 182 |
| 10 | 196 | 257 | 135 | 196 |
| 11 | 187 | 251 | 128 | 187 |
| 12 | 182 | 238 | 121 | 169 |
| 13 | 191 | 256 | 124 | 176 |
| Average | 185 | 245 | 124 | 177 |

The measurements were taken on healthy test persons who had no skin injuries/diseases. Measurements were carried out in an air-conditioned room (T=20-23° C.). Hair was shaved off and the skin first cleaned with a cleaning agent (Bacillol® 25, Bode Chemie, Germany) and dried in the air. As can be seen the inventive jet interruption system in combination with the inventive application system enhances the penetration of substances, in this case microemulsions, through the skin. The jet interruption cycles thus enable the application efficiency to be raised by almost one third.

The invention claimed is:

1. Method for spraying on skin a pharmaceutical or cosmetic active agent-containing composition for transepidermal surface administration, the composition being accommodated in a container that is flow connected with a propellant gas source and spraying device, wherein a first pressurized gas composition is used as propellant that consists of at least 60% v/v of oxygen and wherein the propellant atomizes the composition and, when a spraying device (2) is actuated, forces it out of the spraying device (2) characterized in that the propellant gas forces the composition out of the spraying device (2) in the form of a conical spray jet at an exit velocity of ≥100 m/s at a discharge angle of the spraying device of at least 10° whereby to obtain a spray-covered skin surface of ≥10 cm², and thereafter spraying an oxygen-rich second propellant gas composition for a time span of several minutes on said spray covered skin surface.

2. The method of claim 1 wherein the spraying device comprises a container (1) flow-connected to the spraying device to accommodate the pharmaceutical or cosmetic active agent-containing composition.

3. The method of claim 1 wherein the propellant is from a propellant gas source (3) flow-connected to the spraying device in such a manner that the propellant gas atomizes the sprayable composition and, when the spraying device (2) is actuated, forces it out of the spraying device.

4. The method of claim 1, characterized in that the discharge angle of the spraying device (2) amounts to at least 15°.

5. The method of claim 1, characterized in that the exit velocity amounts to at least 300 m/s.

6. The method of claim 1, characterized in that the spraying device (2) is a de Laval nozzle.

7. The method of claim 1, characterized in that the gage pressure produced by the propellant gas amounts to 1 to 7 bar.

8. The method of claim 7, characterized in that the gage pressure produced by the propellant gas amounts to 2 to 4 bar.

9. The method of claim 1, characterized in that the sprayable composition is a microemulsion, a nanoemulsion, an emulsion, a gel, a microfoam, a liposomes or microbubbles containing composition, a suspension or a dissolution of the active agents in a solvent.

10. The method of claim 1, characterized in that the volume of the sprayable composition in container (1) amounts to 0.2 to 10 ml.

11. The method of claim 10, characterized in that the volume of the sprayable composition in container (1) amounts to 1 to 10 ml.

12. The method of claim 1, characterized in that the amount of propellant gas exiting through outlet opening amounts to 15 to 50 l/min.

13. The method of claim 12, characterized in that the amount of propellant gas exiting through outlet opening amounts to 20 to 30 l/min.

14. The method of claim 1, characterized in that the spray jet driven out of the spraying device (2) is temporarily interrupted.

15. The method of claim 14, characterized in that the spray jet is interrupted at least once.

16. The method of claim 15, characterized in that the spray jet is interrupted several times per second.

17. The method of claim 16, characterized in that the spray jet is interrupted 6 to 14 times per second.

18. The method of claim 17, characterized in that the spray jet is interrupted 8 to 12 times per second.

19. The method of claim 18, characterized in that the spray jet is interrupted approximately 10 times per second.

20. The method of claim 1 characterized in that the propellant gas consists of at least 98% v/v of oxygen.

* * * * *